US00PP30064P2

(12) United States Plant Patent
Verhoef

(10) Patent No.: US PP30,064 P2
(45) Date of Patent: Jan. 8, 2019

(54) ***WEIGELA* PLANT NAMED 'VERWEIG 8'**

(50) Latin Name: *Weigela florida*
Varietal Denomination: Verweig 8

(71) Applicant: Gijsbertus Verhoef, Hazerswoude-Dorp (NL)

(72) Inventor: Gijsbertus Verhoef, Hazerswoude-Dorp (NL)

( * ) Notice: Subject to any disclaimer, the term of this patent is extended or adjusted under 35 U.S.C. 154(b) by 0 days.

(21) Appl. No.: 15/732,426

(22) Filed: Nov. 9, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Weigela florida*, 'Verweig 8', characterized by its vigorous growth habit, its compact plant habit, its free-branching habit, its foliage that is variegated with dark purplish green center and creamy white margins with the young foliage and growth tips tinged with pink, its floriferous and remontant blooming habit, and its flowers that are red-purple in color.

2 Drawing Sheets

Botanical classification: *Weigela florida.*
Variety denomination: 'Verweig 8'.

BACKGROUND OF THE INVENTION

The present invention relates to a new and distinct cultivar of *Weigela* and will be referred to hereafter by its cultivar name, 'Verweig 8'. 'Verweig 8' represents a new cultivar of *Weigela*, a deciduous shrub grown for landscape use.

The new cultivar was discovered by the Inventor on July of 2015 as a naturally occurring branch mutation of *Weigela* 'Verweig' (U.S. Plant Pat. No. 16,824) that was growing outdoors in a trial field in Hazerswoude-Dorp, The Netherlands.

Asexual propagation of the new cultivar was first accomplished by softwood stem cuttings by the Inventor in July of 2015 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Verweig 8' as a unique cultivar of *Weigela.*

1. 'Verweig 8' exhibits a vigorous growth habit.
2. 'Verweig 8' exhibits a compact plant habit.
3. 'Verweig 8' exhibits a free-branching habit.
4. 'Verweig 8' exhibits foliage that is variegated with dark purplish green center and creamy white margins with the young foliage and growth tips tinged with pink.
5. 'Verweig 8' exhibits a floriferous and remontant blooming habit.
6. 'Verweig 8' exhibits flowers that are red-purple in color.

'Verweig', the parent plant of 'Verweig 8', differs from 'Verweig 8' in having a less vigorous growth habit and foliage that is less strongly variegation and more prone to leaf-burn. 'Verweig 8' can also be compared to the *Weigela florida* cultivars 'Nana Variegata' (not patented) and 'Kolmagira' (U.S. Plant Pat. No. 20,384). Both 'Nana Variegata' and 'Kolmagira' are similar to 'Verweig 8' in having variegated foliage. 'Nana Variegata' differs from 'Verweig 8' in having a less compact plant habit, young leaves and growing tips that are not tinged pink in color and leaves that have medium green centers and creamy white to white margins. 'Kolmagira' differs from 'Verweig 8' in having a less compact plant habit and leaves that have medium green centers and light yellow margins.

BRIEF DESCRIPTION OF THE DRAWINGS

The accompanying colored photographs were taken in August and illustrates the overall appearance and distinct characteristics of 28 month-old plants (pruned hard to 10 cm above the soil surface 3 months prior to the description) of the new *Weigela* as grown outdoors in a trial field in Hazerswoude-Dorp, The Netherlands.

The photograph in FIG. 1 provides an overall view of the growth habit of 'Verweig 8'.

Figure 1:
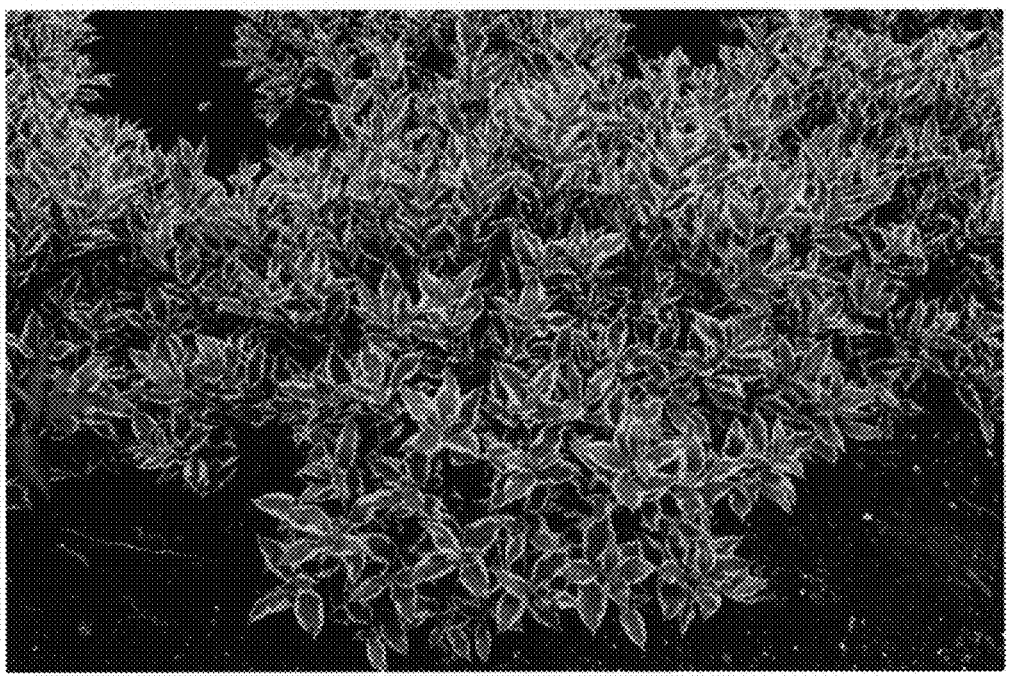
Figure 2:
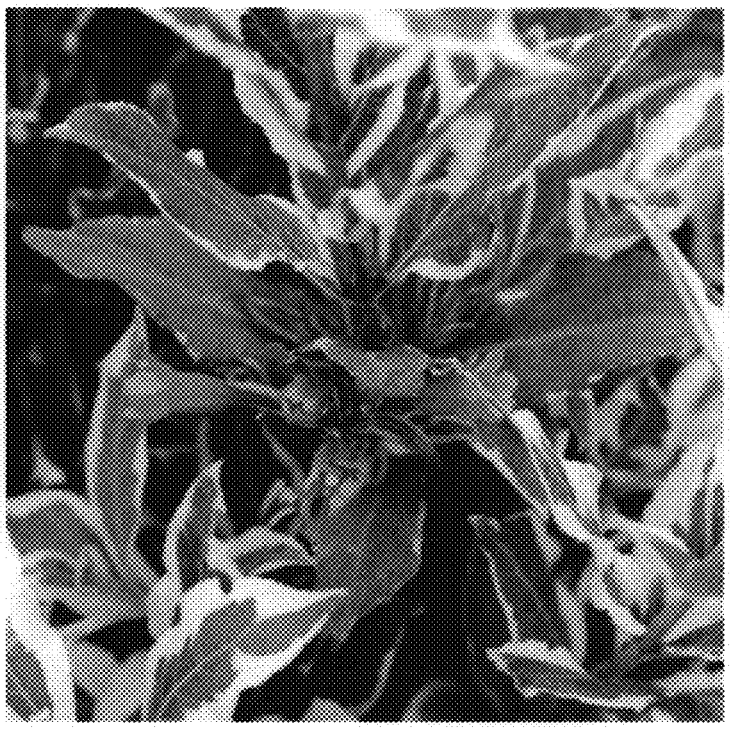

The photograph in FIG. 2 provides a close-up view of the flowers of 'Verweig 8'.

Figure 3:
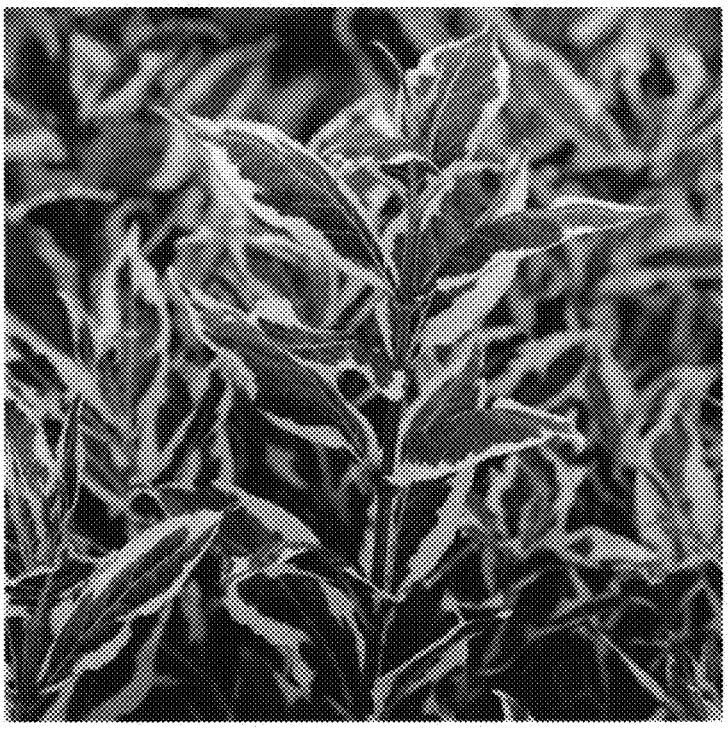

The photograph in FIG. 3 provides a close-up view of the foliage of 'Verweig 8'.

The colors in the photographs may differ slightly from the color values cited in the detailed botanical description, which accurately describe the colors of the new *Weigela*

DETAILED BOTANICAL DESCRIPTION

The following is a detailed description of 28 month-old plants (pruned hard to 10 cm above the soil surface 3 months prior to the description) of the new cultivar as grown outdoors in a trial field in Hazerswoude, The Netherlands. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Blooming period*.—Blooms in late spring (May) and late summer into early fall (August and September) in The Netherlands.

*Plant type*.—Deciduous shrub.

*Plant habit*.—Compact, upright, freely branched.

*Plant size*.—An average of 37.8 cm in height and 73.9 cm in diameter as a 28 month-old plant and 60 cm in height and 125 cm in width as a mature plant in the landscape.

*Cold hardiness*.—At least in U.S.D.A. Zone 5.

*Diseases and pests*.—No susceptibility to resistance to diseases or pests has been observed.

*Root description*.—Fibrous, moderately dense.

*Propagation*.—Softwood stem cuttings.

*Root initiation*.—An average of 6 weeks.

*Root development*.—An average of 3 months to fully develop as a young rooted plant.

*Growth rate*.—Moderately vigorous.

Branch description:

*Branch shape*.—Rounded, young stems slightly angulate with four angles, two of which are slightly more pronounced.

*Branch color*.—New growth; 145A, mature wood; 147D, tinged with 199A, bark; 199A to 199B.

*Branch size*.—An average of 31 cm in length and 3 mm in diameter.

*Branch surface*.—Pronounced angles are densely covered with short adpressed hairs; average of 0.5 cm in length and 156D in color.

*Branch aspect*.—Upright to outward at an average angle of 30°.

*Branch quantity*.—An average of 136 main basal branches and 200 lateral branches.

*Internode length*.—2.7 cm.

Foliage description:

*Leaf shape*.—Obovate to elliptic.

*Leaf division*.—Simple.

*Leaf base*.—Acute.

*Leaf apex*.—Apiculate.

*Leaf fragrance*.—None.

*Leaf aspect*.—Held in an average angle of 45° to lateral branch.

*Leaf venation*.—Pinnate, color upper and lower surface 149B, 147B or 147C.

*Leaf margins*.—Finely serrate.

*Leaf arrangement*.—Opposite.

*Leaf attachment*.—Petiolate.

*Leaf surface*.—Both surfaces are smooth, glabrous and slightly glossy, veins are sparsely covered with very short adpressed hairs; average of 0.2 mm in length and 157D in color.

*Leaf size*.—An average of 6.9 cm in length and 3.3 cm in width.

*Leaf quantity*.—An average of 24 (12 pairs) per lateral branch.

*Leaf color*.—Young leaves upper surface; 200A tinged 147A, leaf broadly and irregularly margined 180C and 180D, young leaves lower surface; 200A tinged 147A, leaf broadly and irregularly margined180D, mature upper surface; color between NN137A and 147A (closest to 147A but darker), leaf broadly and irregularly margined 4D, tip and borders of central blotch tinged 181A, mature lower surface 147A tinged 199A, leaf broadly and irregularly margined 8D, tip and borders of central blotch tinged 181C.

*Petioles*.—Average of 2.5 mm in length, 3 mm in width, flattened, upper surface color N145B, margins 182D, lower surface color 150C, strong, both surfaces are smooth and glabrous with margins sparsely to moderately covered with very short pubescence; 0.3 mm in length and 157D in color.

*Stipules*.—None.

Inflorescence description:

*Inflorescence type*.—Solitary, in pairs, or in small clusters at terminus and leaf axils.

*Inflorescence size*.—3.5 cm in height, 2.8 cm in diameter.

*Flower buds*.—Oblanceolate in shape, an average of 2.2 cm in depth and 6 mm in diameter, 187B in color, matte surface, sparsely covered with very short hairs; an average of 0.2 mm in length, too small to measure color.

*Flower fragrance*.—None.

*Lastingness of flowers*.—About 12 days, self-cleaning.

*Flower aspect*.—Outward to upright.

*Flower quantity*.—An average 3 per inflorescence, 100 buds and flowers per plant.

*Flower type*.—Tubular.

*Flower size*.—Average of 1.2 cm in height, 1.2 cm in diameter, 2.5 cm in depth, throat; 4 mm in diameter, tube; 1.9 cm in length, 3 mm in diameter.

*Peduncles*.—Average of 8 mm in length and 1.5 mm in diameter, held straight on top of lateral branch, moderate strength, dull surface, 147A to 147B in color, slightly angulate with four angles, two of which are slightly more pronounced, pronounced edges are sparsely covered with short hairs; 0.2 mm in length and too small to measure color.

*Calyx*.—Rotate in shape, an average of 9 mm in depth and 5 mm in width.

*Sepals*.—5, rotate, linear in shape, narrowly acute apex, cuneate base, lower 40% fused, entire margin, an average of 9 mm in length and 1.5 mm in width, upper and lower surface is smooth, glabrous and dull, color; when opening and fully open upper and lower surface 194D, tinged with 187B.

*Petals*.—5, lower 75% fused into tube, spathulate in shape, margin entire on free portion, apex obtuse, an average of 2.5 cm in length, 5 mm in width, color; upper and lower surface glabrous and moderately velvety, color; when opening and fully open upper surface 59D, when opening and fully open lower surface 59B to 59C, throat color; 59D, tube color; outer surface 59C, inner surface 187B.

Reproductive organs:

*Gynoecium*.—Pistil; 1, average of 2.6 cm in length, style; average of 2.5 cm in length, and 155B in color, fading towards the proximal end to 186D in color, stigma; club-shaped, 1 mm in length, 1.5 mm in diameter, 160C in color, ovary; 147A and tinged 200A in color.

*Androecium*.—Stamens; 5, filaments; 186D in color and an average of 9 mm in length, implanted in petals, anthers; 155B in color, an average of 3.5 mm in length, 0.5 mm in width, narrowly oblong in shape, pollen; low in quantity and 165C in color.

*Fruit and seed*.—No fruit or seed production has been observed to date.

It is claimed:

1. A new and distinct cultivar of *Weigela* plant named 'Verweig 8' as herein illustrated and described.

* * * * *